(12) United States Patent
Caldwell et al.

(10) Patent No.: US 11,551,573 B2
(45) Date of Patent: Jan. 10, 2023

(54) SMART BOOKLET WITH INTEGRATED BEHAVIOR INCENTIVIZATION AND TRACKING FEATURES

(71) Applicant: Humanity Press, Inc., San Jose, CA (US)

(72) Inventors: John Stewart Caldwell, San Jose, CA (US); Robert de Rooy, Higgovale (ZA); Erica Leigh Boshoff, KwaZulu-Natal (ZA); Aarushi Abraham Karimpanal, San Jose, CA (US); Giles Matthew Lowe, Saratoga, CA (US)

(73) Assignee: Humanity Press, Inc., San Jose, CA (US)

( * ) Notice: Subject to any disclaimer, the term of this patent is extended or adjusted under 35 U.S.C. 154(b) by 343 days.

(21) Appl. No.: 16/823,310

(22) Filed: Mar. 18, 2020

(65) Prior Publication Data

US 2021/0295733 A1 Sep. 23, 2021

(51) Int. Cl.
*G09B 19/00* (2006.01)
*G06N 5/04* (2006.01)
*G06Q 50/20* (2012.01)
*G16H 40/67* (2018.01)
*G16H 20/10* (2018.01)
(Continued)

(52) U.S. Cl.
CPC .............. *G09B 19/00* (2013.01); *A61J 1/035* (2013.01); *G06N 5/04* (2013.01); *G06Q 50/205* (2013.01); *G09B 5/062* (2013.01); *G16H 20/10* (2018.01); *G16H 40/67* (2018.01); *A61J 2205/50* (2013.01)

(58) Field of Classification Search
CPC .......... G09B 19/00; G09B 5/062; G06N 5/04; G06Q 5/205; G06Q 50/205; G16H 20/10; G16H 40/67; A61J 1/035; A61J 2205/50
See application file for complete search history.

(56) References Cited

U.S. PATENT DOCUMENTS 8,737,908 B1 * 5/2014 Smith .................... G09B 5/062
434/317
9,472,113 B1 * 10/2016 Hwang .................. G09B 5/062
(Continued)

OTHER PUBLICATIONS

"STB Product Requirements Document", Humanity Press, 31 pgs.

*Primary Examiner* — Michael Collins
(74) *Attorney, Agent, or Firm* — Schwegman Lundberg & Woessner, P.A.

(57) ABSTRACT

A method of configuring a smart booklet to encourage adherence to a treatment and/or educational program is disclosed, wherein the smart booklet is "off the grid" (e.g., not connected to an electrical or networking grid) and includes an integrated behavior incentivization feature. Based on an activation of a detection feature of the smart booklet, it is detected whether a state of one or more pages of the smart booklet has changed. Based on the determination that the state of the one or more pages has changed, a set of data items pertaining to the adherence to the treatment and/or educational program is created or updated. Based on an identification that the set of data items is indicative of a failure or a success with respect to the adherence to the treatment program, a message pertaining to the failure or the success is communicated via an output component of the smart booklet (e.g., to encourage the adherence to the treatment and/or educational program).

17 Claims, 16 Drawing Sheets

(51) Int. Cl.
*G09B 5/06* (2006.01)
*A61J 1/03* (2006.01)

(56) References Cited

U.S. PATENT DOCUMENTS

| | | | |
|---|---|---|---|
| 9,478,143 B1* | 10/2016 | Bowen | G09B 5/06 |
| 10,375,847 B2 | 8/2019 | Mehregany | |
| 2008/0077429 A1* | 3/2008 | Coe | G06Q 10/10 |
| | | | 600/300 |
| 2013/0189661 A1* | 7/2013 | el Kaliouby | G06Q 30/0271 |
| | | | 434/236 |
| 2016/0063877 A1* | 3/2016 | Javidan | G09B 5/062 |
| | | | 434/317 |
| 2019/0201286 A1 | 7/2019 | Learmonth et al. | |
| 2019/0206538 A1* | 7/2019 | Xing | G16H 10/00 |

\* cited by examiner

SMART BOOKLET WITH INTEGRATED BEHAVIOR INCENTIVIZATION AND TRACKING FEATURES

TECHNICAL FIELD

The present application relates generally to the technical field of educational systems and methods, and, in one specific example, to an interactive smart book system having an integrated feature for incentivizing user behavior.

BACKGROUND

International aid organizations, governments, corporations and individuals worldwide have an urgent need to communicate vital health and life skills information to the billions of people who need it most, despite their vastly different levels of literacy, wealth, or racial and/or ethnic diversity. For example, these entities have an urgent need to not only distribute medicines and track their usage across diverse populations, but also to efficiently provide education to improve the chances of success (e.g., reduction or eradication of illnesses and diseases) of clinical trials or large-scale treatment programs, including those targeting diverse populations.

Other entities operating across a range of industries lack a cheap and configurable option for tracking, educating, or incentivizing behaviors of one or more agents, employees, clients, users, and so on (e.g., with respect to consumption or use of one or more products produced or distributed by the entities).

BRIEF DESCRIPTION OF THE DRAWINGS

Some embodiments are illustrated by way of example and not limitation in the figures of the accompanying drawings.

DETAILED DESCRIPTION

Figure 1:
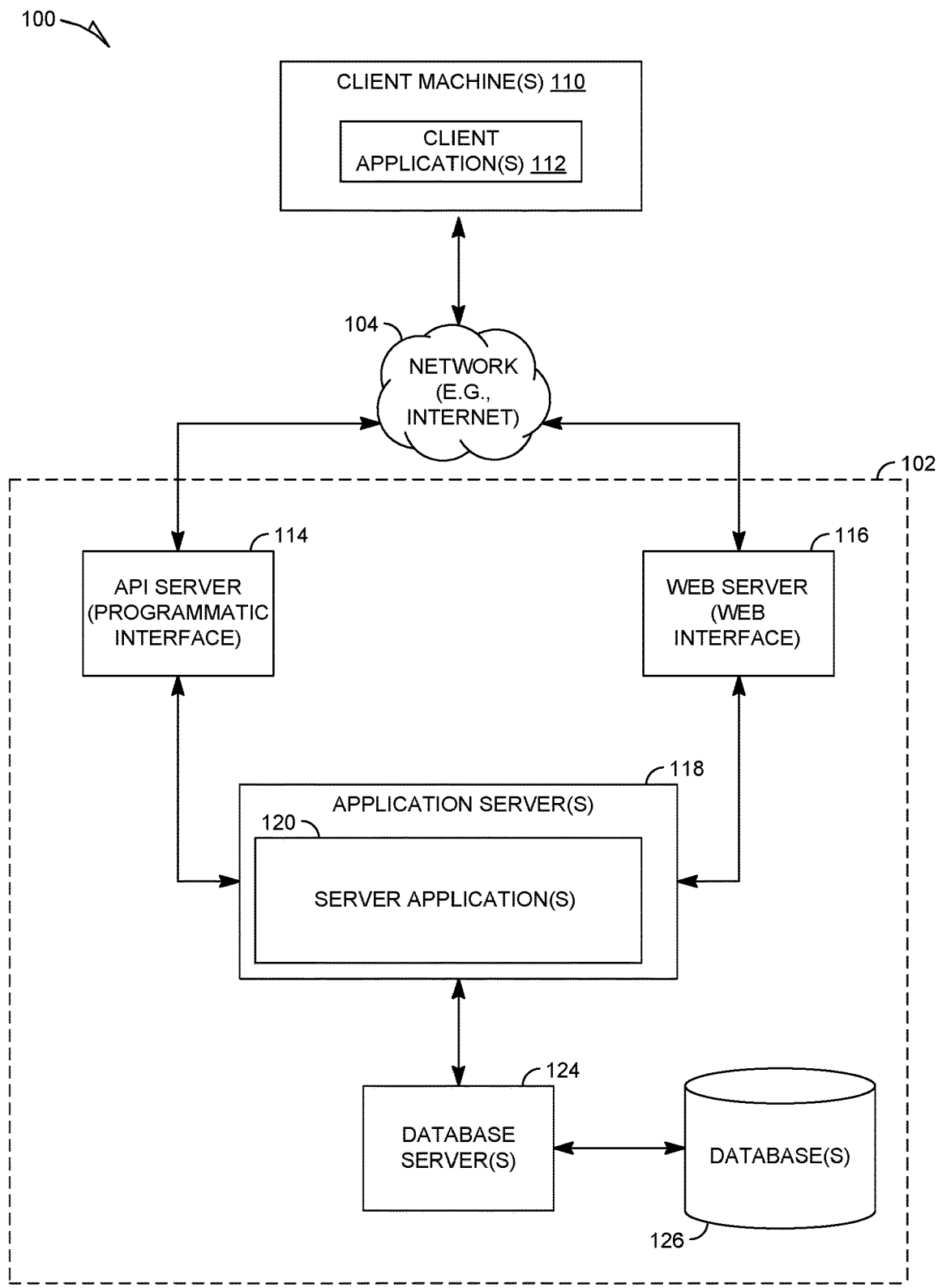
FIG. 1 is a network diagram depicting a client-server system within which various example embodiments may be deployed.

In the following description, for purposes of explanation, numerous specific details are set forth in order to provide an understanding of various embodiments of the present subject matter. It will be evident, however, to those skilled in the art that various embodiments may be practiced without these specific details.

A system and method of configuring a smart book or booklet to encourage adherence to a treatment program is disclosed. Based on an activation of a detection feature of the smart booklet, it is detected whether a state of one or more pages (or aspects, components, or sections) of the smart booklet have changed. For example, it is detected whether one or more medicines (e.g., medicine tablets) have been removed from one or more compartments included in one or more pages or sections of the smart booklet. Or it is detected whether one or more removable tabs (e.g., perforations) have been removed from the one or more pages or sections of the smart booklet. Based on a determination that the state has changed, a set of data items pertaining to the adherence to the treatment program is created or updated. The set of data items is stored in one or more computer memories of the smart booklet. Based on an identification that the set of data items is indicative of a success or a failure with respect to the adherence to the treatment program, a message pertaining to the success or the failure is communicated from an output component of the smart booklet (e.g., information, warnings, instructions, or congratulatory statements pertaining to the adherence that are specially-tailored based on a locale or group or class of users associated with the smart booklet).

In example embodiments, a smart booklet comprises a low-cost, solar powered booklet. In example embodiments, the smart booklet is "off-the-grid." For example, it is not connected to a grid, such as an electrical or communication grid. Furthermore, the smart booklet may consist of one or more components that are selected based on their low cost (e.g., "low-tech"). In this way, the smart booklet may be manufactured inexpensively and distributed for use across diverse populations, including populations lacking convenient access to electricity and the internet. In example embodiments, the smart booklet may include visual information (e.g., included on one or more pages of the smart booklet) and recorded voice data that is designed to supplement the visual information included on the one or more pages. In example embodiments, the smart booklet comprises educational and instructional material, in one or more selectable or pre-selected languages, as well as dynamic content that is presented based on one or more states of one or more pages of the smart booklet, as described in more detail below.

In example embodiments, a smart booklet is configured to play audio content (e.g., via one or more output elements of the smart booklet, such as one or more speakers). In example embodiments, the audio content may include educational information pertaining to a subject of the smart booklet or content included on one or more page of the smart booklet. In example embodiments, such educational information may pertain to adherence to a drug treatment program. In example embodiments, such educational information may pertain to instructions for using or consuming a product. A smart treatment booklet that provides information pertaining to a treatment, such as a drug treatment, may be referred to as a smart treatment booklet (STB). In example embodiments, the audio content is customized (e.g., based on an application of a set of rules to a set of data items collected by the smart booklet pertaining to adherence to the drug treatment program) to include one or more notifications designed to encourage adherence to the drug treatment program. Such customized content may be dynamically presented based on one or more states of one or more pages of the smart booklet.

For example, the notifications may be selected based on various factors, including a result of the application of the set of rules to the set of data items collected, such as a result that indicates a success or a failure to adhere to a drug treatment program and/or educational program (and/or a type of the success or the failure), a locale (or group or class of users) associated with the smart booklet (such as a locale or population of users into which the smart booklet was selected to be distributed), an identification of the page of the smart booklet that is currently open, an identification of one or more states of one or more pages of the smart booklet, and so on. In example embodiments, the playing of the audio content may be triggered by activation of one or more input elements of the smart booklet, such as a touch-sensitive side panel that includes one or more buttons or other activatable components. In example embodiments, some parts of the audio content may be configurable content that corresponds to visual information presented on one or more pages of the smart booklet. In example embodiments, additional parts of the audio content may be configurable content that corresponds to a result of an application of the set of rules. In example embodiments, the type of the success or failure may be identified based on application of the set of rules. For example, a type of a failure may include a failure to take one or more medicines within a prescribed time period specified by the rules. The application of the set of rules may further identify one or more notifications that are to be communicated to allow a user to remedy the failure, such as a message to take one or more additional medicines or otherwise modify the treatment and/or educational program. The rules and notifications may be selected based on statistical data pertaining to their effectiveness, as explained in more detail below. In this way, application of the set of rules may effectively modify a treatment and/or educational program to improve a probability that a user will adhere to the treatment program.

In example embodiments, the notifications are standardized and configurable (e.g., by a customer or educator) for use with various languages and/or to incorporate culture-specific stories or characters to assist in conveying the educational information. Thus, the educational information is adaptable to convey common health or public educational themes in a manner that is identified as being appropriate and/or effective for a particular locale (or group or class of users) to which the smart booklet is distributed, including based on demographics (e.g., age, gender, level of educational attainment, economic factors, such as level of impoverishment, and so on) of users targeted by the smart booklet.

In example embodiments, the set of data items pertaining to the adherence is created or updated based on a detection of whether one or more medicines (or one or more removable tabs) have been removed from one or more compartments included in one or more pages of the smart booklet, the set of data items being stored in one or more memories of the smart booklet. In example embodiments, the detection of whether the one or more medicines (or one or more tabs) have been removed from the one or more compartments is triggered based on an activation of a detection element of the smart booklet. For example, the detection element may be triggered by the closing of the smart booklet or a closing of a page of the smart booklet. Or the detection element may be triggered automatically at a configurable, periodic time interval. In example embodiments, the detection is based on a metal detecting element of the smart booklet detecting that one or more metal portions of the one or more compartments of the medicine-containing portion of the smart booklet have been removed (e.g., thus suggesting that the medicines included in the compartment have also been removed).

Thus, in example embodiments, educational content may be conveyed using culturally relevant stories and/or information in combination with interactive spoken audio features. Such educational content may include important messages regarding health, life skills, job training, and drug treatments.

In an example embodiment, the educational material pertains to maintenance or consumption of a product. For example, consider one or more maintenance procedures that are required to be performed on a water well by a maintenance crew. The educational material may include step-by-step instructions for performing the one or more maintenance procedures. To indicate successful completion of a maintenance procedure (e.g., such a completion of a procedure that is to be completed periodically, such as every six months), the maintenance crew may remove a perforated tab from the booklet. A sensor of the booklet may detect that the tab has been removed and then update a set of data items pertaining to the completion of the maintenance procedure, such as a date or time of the completion, a type of maintenance performed, and so on. For example, based on the successful completion of one or more procedures, a new set of step-by-step instructions may be selected (e.g., from multiple sets of instructions stored in one or more memories of the smart booklet) for presentation to the next maintenance crew. In this way, the instructions that are presented via the smart booklet are based on a set of maintenance rules and a current state of maintenance (e.g., including successful completions of maintenance procedures within a particular maintenance window), such that each subsequent maintenance crew has convenient access to the next maintenance steps that are to be performed. This monitoring and tracking technique can be extended to any type of monitoring or tracking, such as for consumption of goods, especially for which off-the-grid capabilities This method and various operations disclosed herein may be implemented as a computer system having one or more modules (e.g., hardware modules or software modules) that are specially designed and incorporated into one or more memories of the computer system to perform these methods or one or more of the operations described herein. These methods and operations disclosed herein may be embodied as instructions stored on a machine-readable medium that, when executed by a machine, cause the machine to perform the method or the one or more operations.

FIG. 1 is a network diagram depicting a system 100 within which various example embodiments may be deployed. A networked system 102, in the example forms of a network-based dosage-tracking system, drug treatment management system, task completion tracking system, and/or clinical trials management system, provides server-side functionality, via a network 104 (e.g., the Internet or Wide Area Network (WAN)) to one or more clients machines 110. FIG. 1 illustrates client application(s) 112 on the client machines 110. Examples of client application(s) 112 may include a web browser application, such as the Internet Explorer browser developed by Microsoft Corporation of Redmond, Wash. or other application supported by an operating system of the device, such as Windows, iOS or Android operating systems. Each of the client application(s) 112 may include a software application module (e.g., a plug-in, add-in, or macro) that adds a specific service or feature to a larger system.

An API server 114 and a web server 116 are coupled to, and provide programmatic and web interfaces respectively to, one or more application servers 118. The application servers 118 host one or more server application(s) 120. The application servers 118 are, in turn, shown to be coupled to one or more database servers 124 that facilitate access to one or more databases 126 or data stores, such as NoSQL or non-relational data stores.

The server applications 120 may provide a number of functions and services to users that access the networked system 102. While the server applications 120 are shown in FIG. 1 to form part of the networked system 102, in alternative embodiments, the various server applications 120 may form part of a service that is separate and distinct from the networked system 102.

Further, while the system 100 shown in FIG. 1 employs a client-server architecture, various embodiments are, of course, not limited to such an architecture, and can equally well find application in a distributed, or peer-to-peer, architecture system, for example. The various server applications 120 can also be implemented as standalone software programs, which do not necessarily have networking capabilities. Additionally, although FIG. 1 depicts client machines 110 as being coupled to a single networked system 102, it will be readily apparent to one skilled in the art that client machines 110, as well as client applications 112, may be coupled to multiple networked systems, such as payment applications associated with multiple payment processors or acquiring banks (e.g., PayPal, Visa, MasterCard, and American Express).

Web applications executing on the client machine(s) 110 may access the various server applications 120 via the web interface supported by the web server 116. Similarly, native applications executing on the client machine(s) 110 may access the various services and functions provided by the server applications 120 via the programmatic interface provided by the API server 114. Examples of server application(s) 120 may be a treatment facilitation program, a clinical trials facilitation program, or an educational distribution system, as described herein. One example of a client application may be a smart book usage tracking system, as described herein. Other examples of client application(s) 112 may be third-party applications. For example, the third-party applications may, utilizing information retrieved from the networked system 102, support one or more features or functions on a website hosted by the third party.

Figure 2:
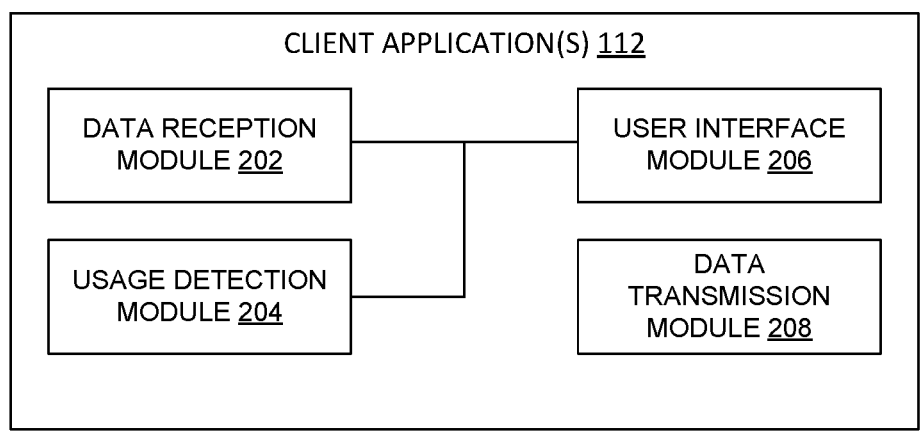
FIG. 2 is a block diagram illustrating example modules of the client application(s) of FIG. 1.

FIG. 2 is a block diagram illustrating example modules of the client application(s) 112. A data reception module 202 is configured to receive data, including programming of content items for presenting by the smart booklet and rules pertaining to triggering of the presenting of the content items (e.g., based on detected usages of the smart booklet), as described. A usage detection module 204 is configured to detect usages of the smart booklet, as described herein. A user interface module 206 is configured to present information via the smart booklet (e.g., by playing audio content items over a speaker of the smart booklet). A data transmission module 208 is configured to transmit data collected and stored in the smart booklet, such as data pertaining to usages of the smart booklet, to an external system for analysis.

Figure 3:
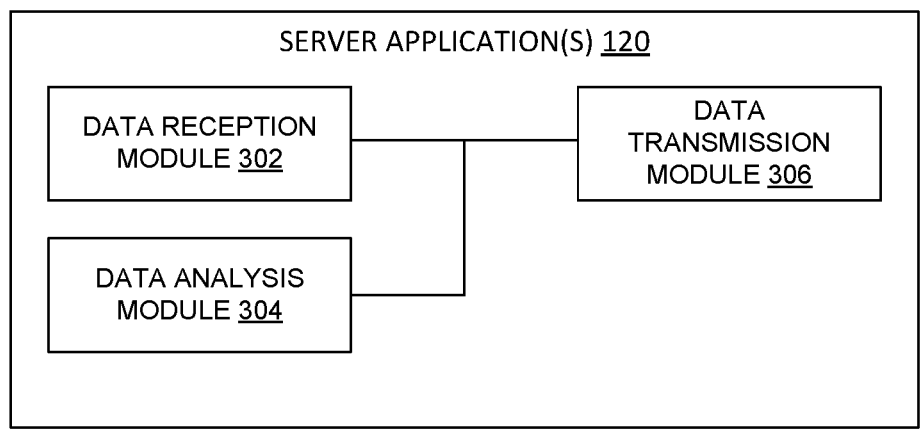
FIG. 3 is a block diagram illustrating example modules of the server application(s) of FIG. 1.

FIG. 3 is a block diagram illustrating example modules of the server application(s) 120. A data reception module 302 is configured to receive data from one or more smart booklets, including data pertaining to usages of the smart booklets. A data analysis module 304 is configured to perform statistical analyses of the received data (e.g., to identify an effectiveness of various combinations of content items presented on the smart booklet) and to evaluate and implement rules included on the device pertaining to the presenting of the content items, such as with respect to an effectiveness in encouraging particular usages of the smart booklet pertaining to drug treatments or clinical trials. A data transmission module 306 is configured to transmit content items and/or rules, including content items and/or rules that have been updated based on the statistical analysis, for storing in one or more smart booklets. In example embodiments, the content items and/or rules are customizable based on locale (or user group or class) data associated with the one or more smart booklets, as described herein.

Figure 4:
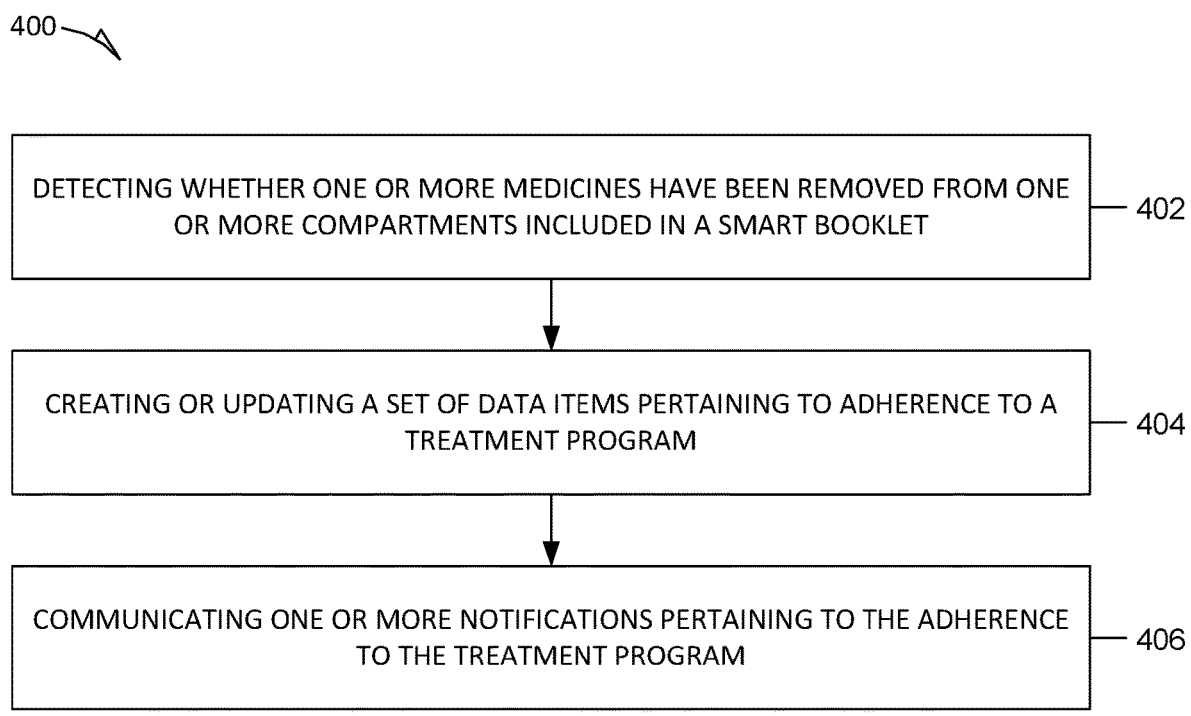
FIG. 4 is a flowchart illustrating example operations of a method of configuring a smart booklet to encourage adherence to a treatment program.

FIG. 4 is a flowchart illustrating example operations of a method 400 of configuring a smart booklet to encourage adherence to a treatment and/or educational program. In example embodiments, the operations may be performed by one or more modules of the client application(s) 112.

At operation 402 it is detected whether one or more medicines (or one or more tabs) have been removed from a smart booklet. In example embodiments, one or more medicines, such as one or more tablets of the one or more medicines, may be included in one or more compartments of the smart booklet, which, in turn, may be included in one or more pages or sections of the smart booklet. In example embodiments, one or more tabs (e.g., not including medicine) may be included in one or more pages of the smart booklet. In example embodiments, the detecting is triggered by, for example an activation of a sensing component of the smart booklet. In example embodiments, the sensing component may be configured to recognize a change of a state of one or more pages of the smart booklet, such as the presence or position of a medicine-containing compartments within a medicine-containing blister pack. In example embodiments, the detecting is based on data received from one or more sensors that are indicative of the one or more medicines having been removed from the smart booklet. For example, a metal-detecting sensor included in the smart booklet may detect that a metal portion has been altered or removed from a compartment in which the one or more medicines are stored in a section or page of the smart booklet. In example embodiments, the metal portion comprises a foil backing that is punched out from a blister pack that is included in the section or the page of the smart booklet. A detection that this metal portion has been removed or modified may be interpreted as indicative that the one or more medicines that were stored in a compartment of the blister pack have been removed from the smart booklet. In example embodiments, an inductive sensor grid inside a housing of the smart booklet senses where metal portions (e.g., corresponding to compartments of a blister pack) have been removed, modified, or disturbed. In example embodiments, the sensing may be triggered when the blister pack is placed back into the housing after having been removed from the housing, such as when the page or section of the smart booklet closed or when the smart booklet itself is closed. Or the sensing may be triggered periodically (e.g., every N number of seconds, where N is a configurable number).9

In example embodiments, the smart booklet may include a first set of sensors, each of which is capable of reading a state of one or more locations of an insertable page or card (e.g., a blister pack). In example embodiments, each sensor may be an inductive sensor that can read seven locations (e.g., corresponding to four seven-day weeks; thus, four sensors can be used to read the state of location corresponding to each day of a four week period. In example embodiments, the smart booklet may include a mounting or binding location for insertion of the one or more removable pages or cards into the smart booklet. Each of the one or more pages or cards may have an edge that is used for connecting to the mounting of the smart booklet and a foldable portion or crease that is used for bending the page or card such that it can be effectively used as a page of the smart booklet. In example embodiments, the edge of each page has an area in which a set of removable tabs or perforations are included. In example embodiments, an additional sensor is added to the smart booklet for reading a pattern of perforations (or removed tabs) included in the edge of the page (e.g., a smart strip, such as the smart strip 1314 depicted in FIG. 13) that is connected to the mounting location. In example embodiments, the pattern of perforations represents data pertaining to the page, such as a type of medicine included in the page, a phase or week of a treatment and/or educational plan with which the page is associated, a locale (or class or group of users) to which the page applies, a language of the target users, and so on. In example embodiments, the patterns of perforations are made during manufacturing of the page or card. In other embodiments, the perforations can be made or the tabs removed (e.g., by a field worker) after manufacturing of the card or page. In example embodiments, a configurable data table corresponding to information elements represented by each possible pattern of perforations is included in one or more memories of the smart booklet. For example, based on an identifier included in the smart strip, the smart booklet may automatically detect whether a card includes medicine for a first week, a second week, or a third week of a TB treatment plan, adjusting any content presented to the user accordingly.

In example embodiments, in order to preserve battery life, the detecting features of the smart booklet are asleep until a button of the smart booklet is activated. In example embodiments, one of the multiple sensors are continually active for the purpose of detecting (e.g., every second) whether the smart booklet has been opened (e.g., to a particular page). Upon opening of the book, a welcome notification may be presented to the user, the welcome notification pertaining to a current state of the page of the booklet, such as which day of treatment the user is on or a stage of a process that the user should be completing. In example embodiments, all but one of the sensors is automatically deactivated after a configurable period of time elapses. After the configurable time period elapses, a notification (e.g., a tone) may be played (e.g., to remind the user to close the booklet). When the smart booklet is closed, the state of the page upon the closing is compared with the state of the page upon the opening of the booklet. Differences in the state are recorded and checked against one or more configurable rules to determine whether a notification should be generated pertaining to the usage of the smart booklet, as described herein.

At operation 404, a set of data items pertaining to adherence to the treatment and/or educational program is created or updated. The set of data items may include, for example, a date, and/or time, and/or a location of a detection of each removal of the one or more medicines (or one or more tabs) from the smart booklet. In example embodiments, the set of data items may include only information that has changed in the set of data items since the set of data items was last updated. In example embodiments, the creating or updating of the set of data items may be triggered by a detection of a change in state of the smart booklet (e.g., a detection that one or more medicines (or one or more tabs) have been removed from the smart booklet). In example embodiments, the set of data items is stored or updated in one or more memories of the smart booklet.

At operation 406, one or more notifications are communicated pertaining to the adherence to the treatment and/or educational program. In example embodiments, based on an identification that the set of data items is indicative of a success or a failure of the adherence to the treatment program, a congratulating for or an encouraging of the adherence to the treatment program is performed. The performing of the congratulating for or the encouraging of the adherence includes communicating a notification via an output component (e.g., a speaker and/or a display) of the smart booklet. In example embodiments, the notification includes one or more of educational information, warnings, or instructions pertaining to the adherence that are specially-tailored based on a locale (or class or group of users) associated with the smart booklet, such as a locale into which the smart booklet was designed or known to have been distributed, and/or a unique profile of the user. In example embodiments, a determination or identification that the set of data items is indicative of the success or failure of the adherence to the treatment program is based on an application of a set of rules to the set of data items, the set of rules pertaining to the adherence to the treatment program, the set of rules being stored in the one or more memories of the smart booklet. In example embodiments, the notification is selected from a plurality of notifications included in the one or more memories based on an identification of a type of the failure of the adherence to the treatment program and a determination of a locale (or class or group of users) to which the smart booklet was designed to be distributed. In example embodiments, the notification includes one or more messages of congratulations or positive reinforcement based on a determination or identification that the set of data items is indicative of a success of the adherence to the treatment program. Notifications communicated via an output (e.g., a speaker) of the smart booklet may be specially-tailored for a user (e.g., based on information pertaining to the locale, a class of patients, language, gender, treatment, or stage of treatment associated with the smart booklet or a location into which the smart booklet as known to have been distributed, as described herein). In example embodiments, the locale may be determined by a geo-tracking sensor included in or associated with the booklet or a matching of a unique identifier of the smart booklet (or of a removable page of the smart booklet) to the locale into which the smart booklet was known to have been distributed.

Figure 5:
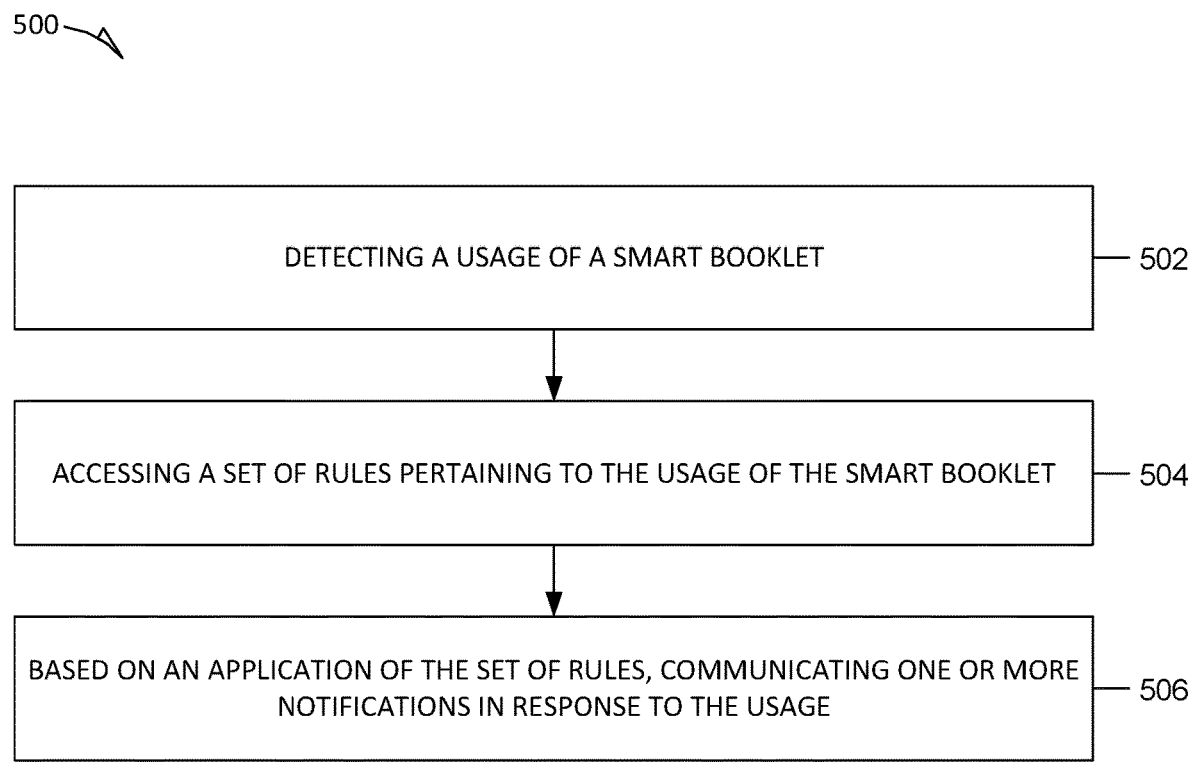
FIG. 5 is a flowchart illustrating an example method of communicating one or more notifications in response to a usage of a smart booklet.

FIG. 5 is a flowchart illustrating an example method 500 of communicating one or more notifications in response to a usage of a smart booklet. In example embodiments, the operations may be performed by one or more modules of the client application(s) 112.

At operation 502, the usage of the smart booklet is detected. For example, one or more sensors of the smart booklet may be configured to detect one or more of an opening or closing of the book, a turning of a page of the book, a flipping to a particular page or section of the smart booklet (e.g., via a tab associated with the page), an opening or closing of a flap included in a page or section (e.g., a flap containing a blister pack of medicines), a change of a state of one or more pages of the smart booklet, and so on. As another example, one or more mechanically-operable components, such as buttons or switches, may be interacted with to engage a functionality of the smart booklet (e.g., to turn the smart booklet on or off, cause audio data associated with a current state of the book (e.g., corresponding to an open page) to be played, to adjust the volume of the audio playback, and so on.

At operation 504, a set of rules pertaining to the usage of the smart booklet is accessed (e.g., from one or more memories of the smart booklet). Such rules may pertain to selection of a notification to be played in response to a detected change in the state of the book (e.g., based on one or more medicines or tabs being removed from the book) or in response to a lack of a change in the state of the book to be detected (e.g., when such a change is expected in order for a treatment program to be complied with). In example embodiments, the set of rules are customizable (e.g., based on communications with an external system, as described herein). In example embodiments, the set of rules specify an action that is to be performed by the smart booklet in response to the detected usage of the smart booklet.

At operation 506, one or more actions are performed by the smart booklet in response to the detected usage of the smart booklet. For example, based on a determination that one or more medicines or tabs have been removed from the smart booklet, a notification pertaining to adherence with a treatment plan is communicated via an output component of the smart booklet, such as a speaker. In example embodiments, the notification is tailored based on a locale (or class or group of users) associated with the smart booklet, or the unique profile of the user.

Figure 6:
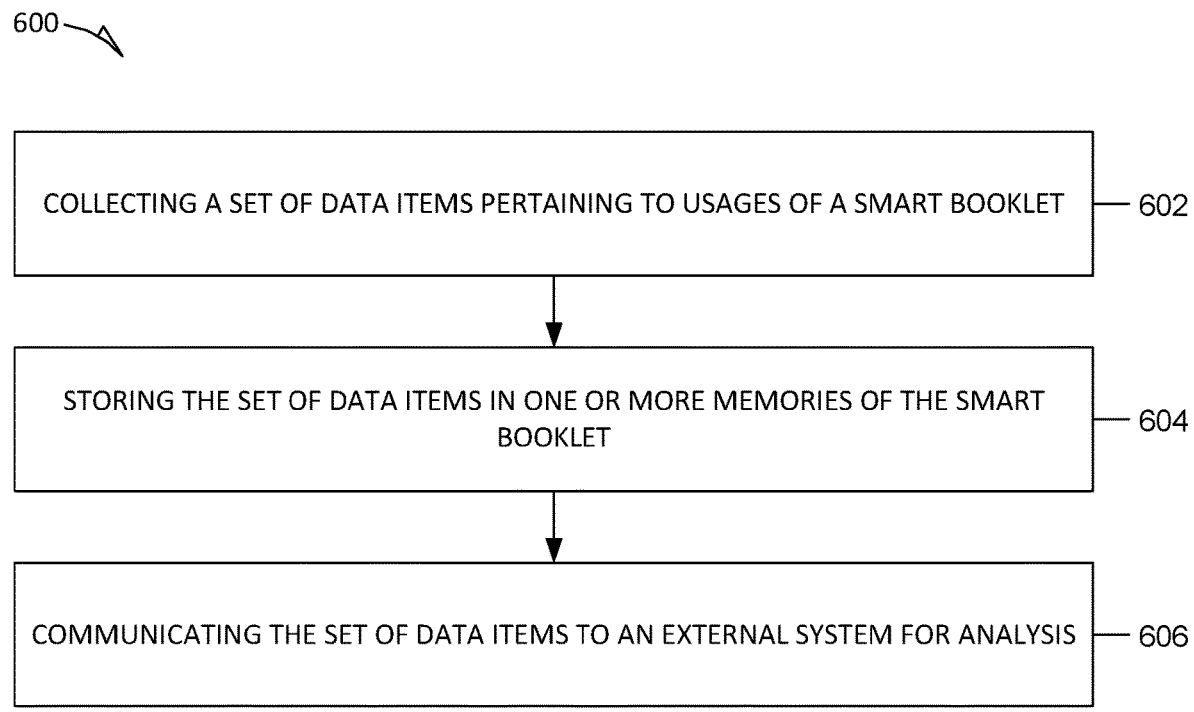
FIG. 6 is a flowchart illustrating an example method of communicating a set of data items pertaining to usages of a smart booklet to an external system for analysis.

FIG. 6 is a flowchart illustrating an example method 600 of communicating a set of data items pertaining to usages of a smart booklet to an external system for analysis. In example embodiments, the operations may be performed by one or more modules of the client application(s) 112.

At operation 602, a set of data items pertaining to usages of the smart booklet are collected. For example, information pertaining to any of the usages discussed herein are collected, such as information pertaining openings or closings pages or sections of the smart booklet, openings or closings of the smart booklet itself, activations of one or more mechanical features to trigger playbacks of one or more audio content items, identifications of one or more pages that were open when the audio content was played, a number of automatic playbacks of content items, conditions under which the automatic playbacks were performed, a state of the book at times of detected usages (e.g., which medicines have been removed from the smart booklet), and so on.

At operation 604, the set of data items is stored in one or more memories of the smart booklet. Such storing may include creating new data items or updating existing data items.

At operation 606, the collected set of data items is communicated to an external system for analysis (e.g., one of the server applications 120). In some embodiments, communications may be output from a port of the smart booklet, such as a USB, mini-USB, or network port. Alternatively, communications may comprise telephonic communication of the set of data items, wherein the telephonic communication includes outputting a set of tones via a speaker of the smart booklet, the set of tones representing values corresponding to the set of data items. In other words, the collected set of data items may be communicated to the external system without having to mechanically connect the smart booklet to another device, such as a network device.

Figure 7:
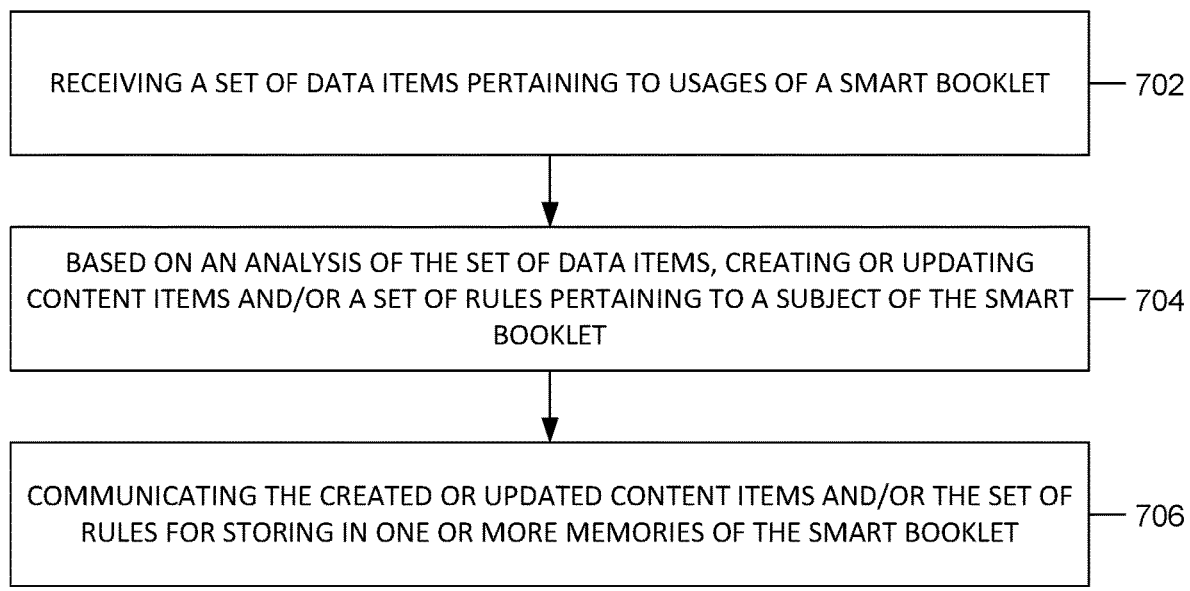
FIG. 7 is a flowchart illustrating an example method of communicating a set of data items pertaining to usages of a smart booklet to an external system for analysis.

FIG. 7 is a flowchart illustrating an example method 700 of communicating a set of data items pertaining to usages of a smart booklet to an external system for analysis. In example embodiments, the operations may be performed by one or more modules of the server application(s) 120.

At operation 702, a set of data items pertaining to usages of a smart booklet are received. The set of data items may include any of the information that is collected by the smart booklet as described herein.

At operation 704, based on an analysis of the set of data items, content items to be presented on the client device (e.g., audio content) and/or one or more rules pertaining to the presenting of the content items on the client device are created or updated. For example, an analysis of the effectiveness of the rules and content items are evaluated in comparison to similar rules and content items received from other smart booklets. For example, statistical analyses may be performed on a large set of data items, such as sets of data items received from thousands or hundreds of thousands of smart booklets. Based on a determination that a first set of rules and/or particular audio content are working better (e.g., in terms of adherence to a treatment plan) in various locales (or with respect to groups or classes of users than a second set of rules and/or audio content, the first set of rules and/or audio content may be selected for inclusion in smart booklets that have already been distributed (e.g., through an updating of the smart booklets) or in smart booklets that have yet to be distributed in a particular locale (or to a particular group or class of users).

At operation 706, the created or updated content items and/or the set of rules are communicated from the external system for storing in the smart booklet or one or more additional smart booklets. In example embodiments, the updating of a smart booklet may be performed through various means, including via a port, such as via a USB, Wi-Fi, Bluetooth, or other network port, or through audio transmission over a telephone line to an audio receiver included in the smart booklet.

Figure 8:
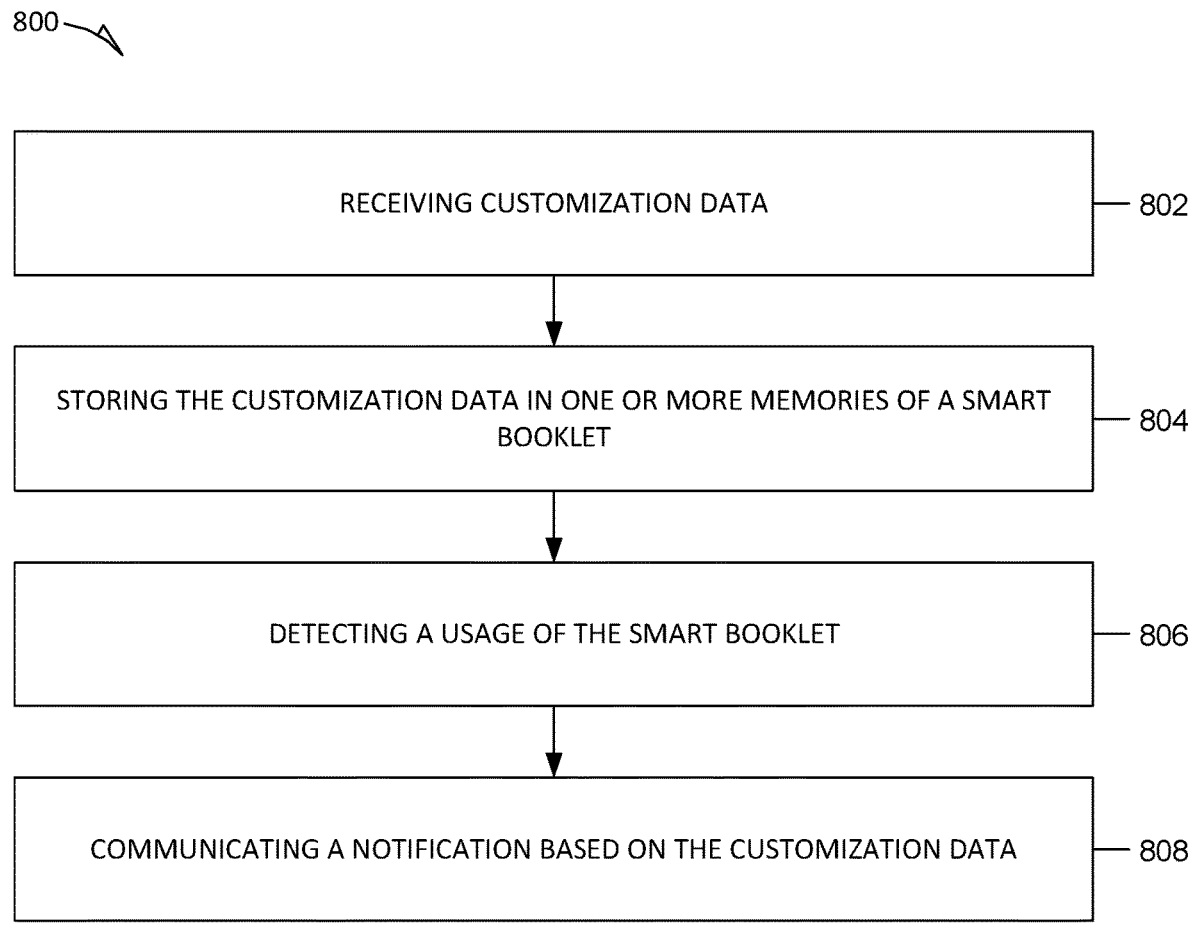
FIG. 8 is a flowchart illustrating an example method of configuring a smart booklet with customization data.

FIG. 8 is a flowchart illustrating an example method 800 of configuring a smart booklet with customization data. In example embodiments, the operations may be performed by one or more modules of the client application(s) 112.

At operation 802, customization data is received. In example embodiments, the customization data corresponds to one or more standardized content items, such as instructions, warnings, encouragement, or other types of notifications described herein. In example embodiments, the customization is selected through an analysis of effectiveness of the customization data in encouraging intended usage of the smart booklet, such as usage pertaining to adherence to a drug treatment program or facilitation of a clinical trial. In example embodiments, the customization data is selected based on a locale (or with respect to a group or class of users) into which the smart booklet is designed to be distributed or known to be distributed (e.g., based on GPS data).

At operation 804, the customization is stored in one or more memories of the smart booklet. For example, the smart booklet is connected (e.g., via a port, such as a USB, Wi-Fi, Bluetooth, or other network port) to a network for transmission of the data over the network. Or the smart booklet receives audio signals via an audio input device (e.g., via a telephone line).

At operation 806, a usage of the smart booklet is detected, as described herein.

At operation 808, a notification is communicated via an output component of the smart booklet. For example, an audio content item is played over a speaker of the smart booklet. In example embodiments, the notification is selected based on application of the set of rules to a detected usage of the smart booklet, as described herein.

Figure 9:
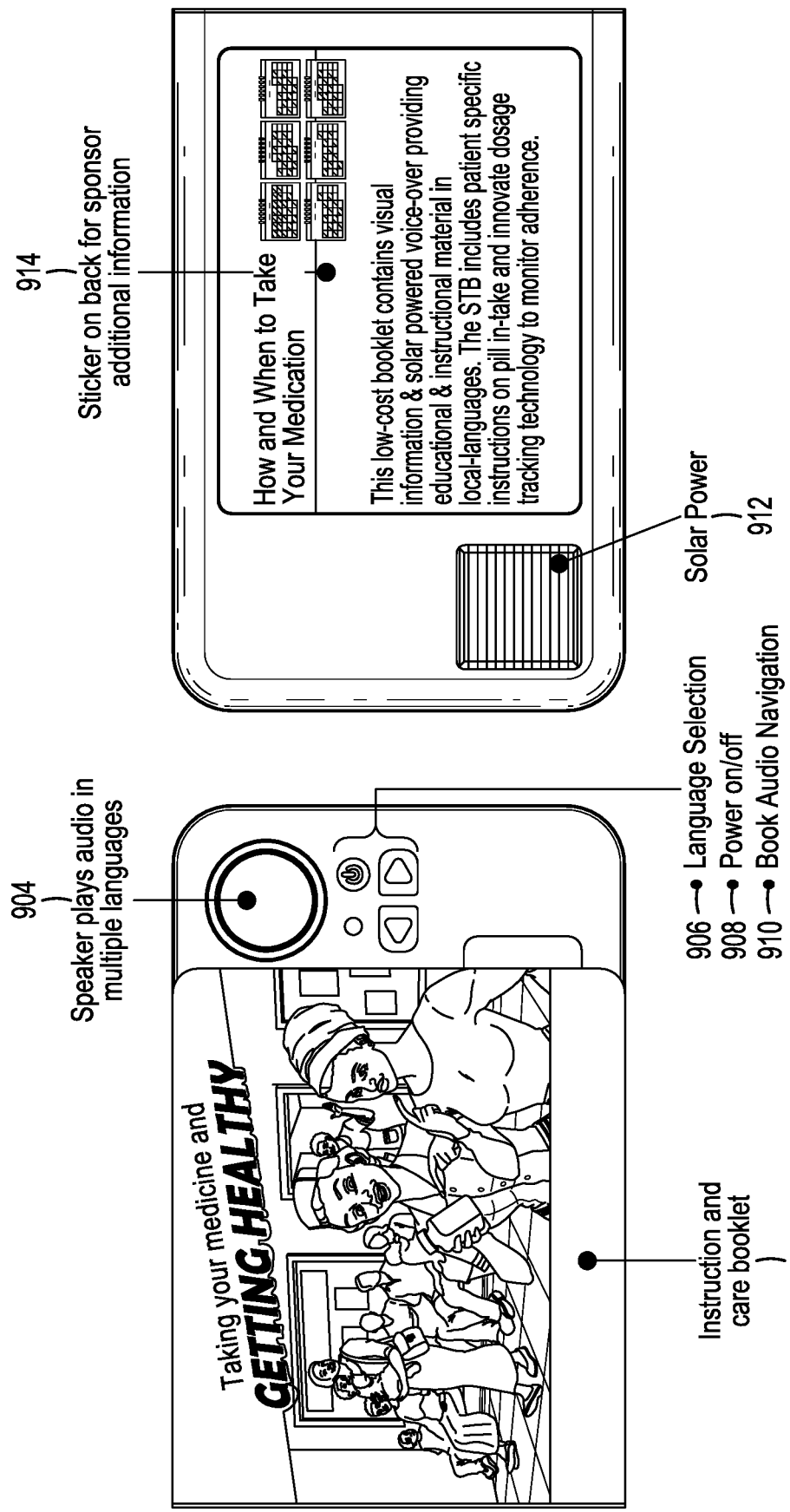
FIG. 9 is a graphical depiction of an example design of a smart booklet.

FIG. 9 is a graphical depiction of an example design of a smart booklet. The smart booklet may include an instruction and care booklet 902 that includes instructions pertaining to a subject of the smart booklet, such as maintenance instructions or medicine (e.g., table) dosage or in-take and instructions (e.g., in pictorial form). The booklet may be further configured with audio content that corresponds to the content of instruction and care booklet 902 and that is tailored for one or more target audiences of the smart booklet (e.g., based on language or culture), enabling even an illiterate user to comprehend the content of the instruction and care booklet. For example, audio content may be stored on one or more memories of the smart booklet and activated (e.g., based on a mechanical operation of the book audio navigation buttons 910). In addition, the smart booklet may include one or more audio instructions that are caused to be presented based on a state of the smart booklet and/or information specific to the smart booklet or a user of the smart booklet, such as a state of a removable blister pack or card that has been inserted into the smart booklet, as explained herein. Thus, appropriate audio content may be selected and caused to be played (e.g., via speaker 904) automatically based on a detected change to a state of the smart booklet (e.g., to encourage adherence to a treatment plan or other step-by-step procedure, as described herein. Furthermore, data items pertaining to usage of the smart booklet (e.g., activation of mechanical buttons 906, 908, and 910, insertion/removal of a blister pack or card, or opening or closing of the booklet or pages of the booklet, and so on) may be monitored and stored in the one or more memories. Such data items may include a count of each of the actions performed and a sequential tracking of changes in the state of the smart booklet and/or deltas in the states of the smart booklet at configurable time intervals or upon occurrence of an event (e.g., opening or closing of the book or a page of the book). In example embodiments, audio content items may be stored in multiple languages (e.g., that are selectable using the language selection button 906). In example embodiments, the smart booklet includes the speaker 904 (e.g., for playing audio content in any of the multiple languages), an instruction and care booklet, and one or more tabs for accessing particular sections of the smart book, such as one or more pages providing for distribution of one or more tablets of one or more medicines. In example embodiments, the smart booklet includes one or more of the language selection button 906, the power on/off switch 908, and the book audio navigation buttons 910. In example embodiments, the smart booklet includes a solar power panel 912, thus enabling electronic features of the book to be operated indefinitely without the smart booklet being connected to an external or finite power source. In example embodiments, the smart booklet includes one or more reserved spaces 914 for graphics or one or more stickers that include information pertaining to adherence to a treatment program, unique identifiers of the STB (bar codes, QR codes or unique QR codes) as well as sponsor logos and information.

Figure 10:
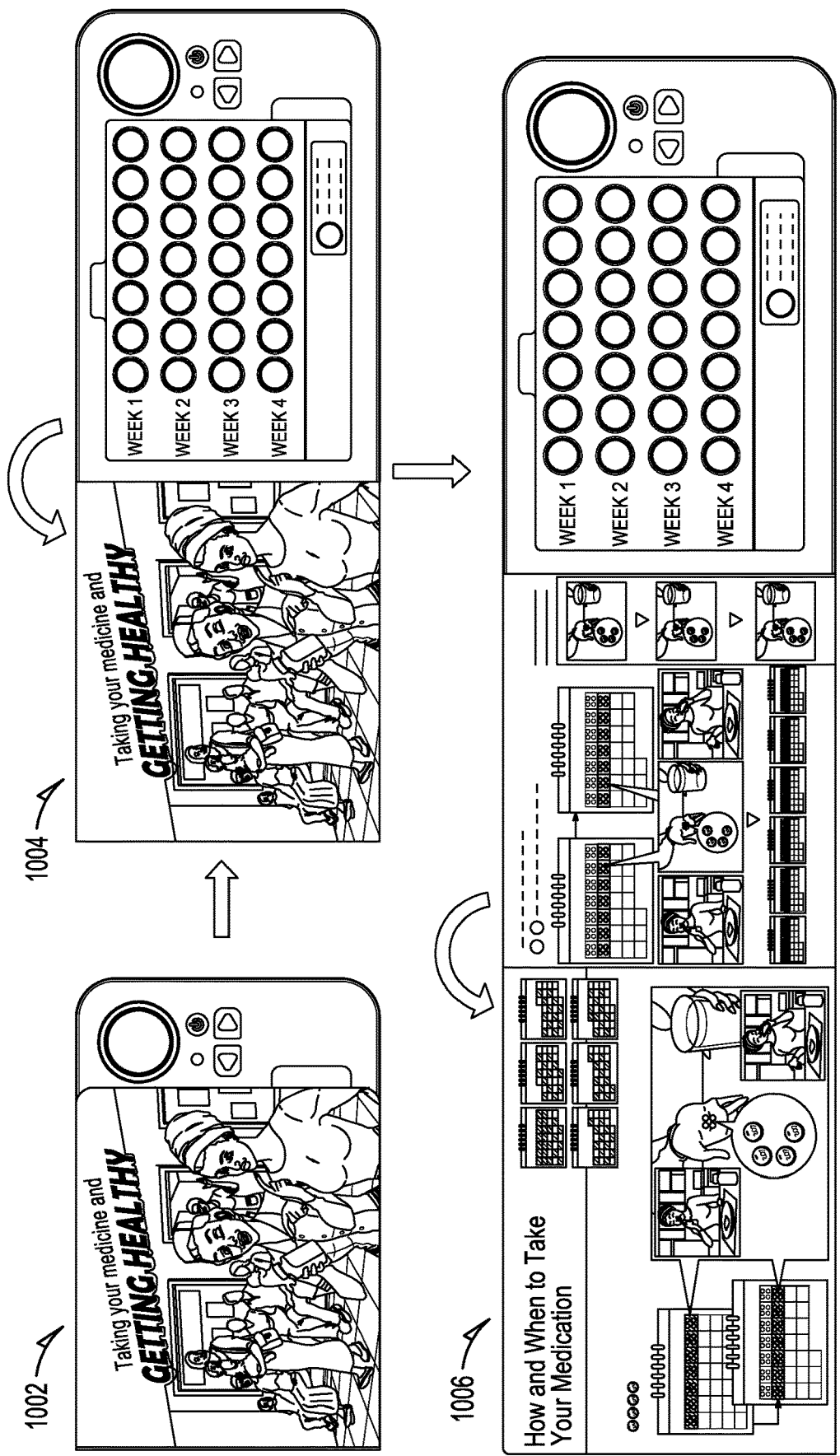
FIG. 10 is a graphical depiction of an example design of illustrated content included on pages of a smart booklet.

FIG. 10 is a graphical depiction of an example design of illustrated content included on pages of a smart booklet. In example embodiments, the illustrated content may include step-by-step instructions, warnings, and/or care information (e.g., in pictorial form). In example embodiments, the illustrated content may be associated with corresponding audio, which may be played through one or more speakers of the smart booklet (e.g., based on activation of one or more input components of the smart booklet, as described herein). In example embodiments, the illustrated content includes a cover page 1002 that is openable to reveal a platform of the smart booklet into which a blister pack or card may be inserted, and one or more additional pages 1006 including pictorial representations of steps that are to be performed. Thus, the steps that are the subject of the smart booklet may be conveyed to a person regardless of the person's known languages or level of literacy.

Figure 11:
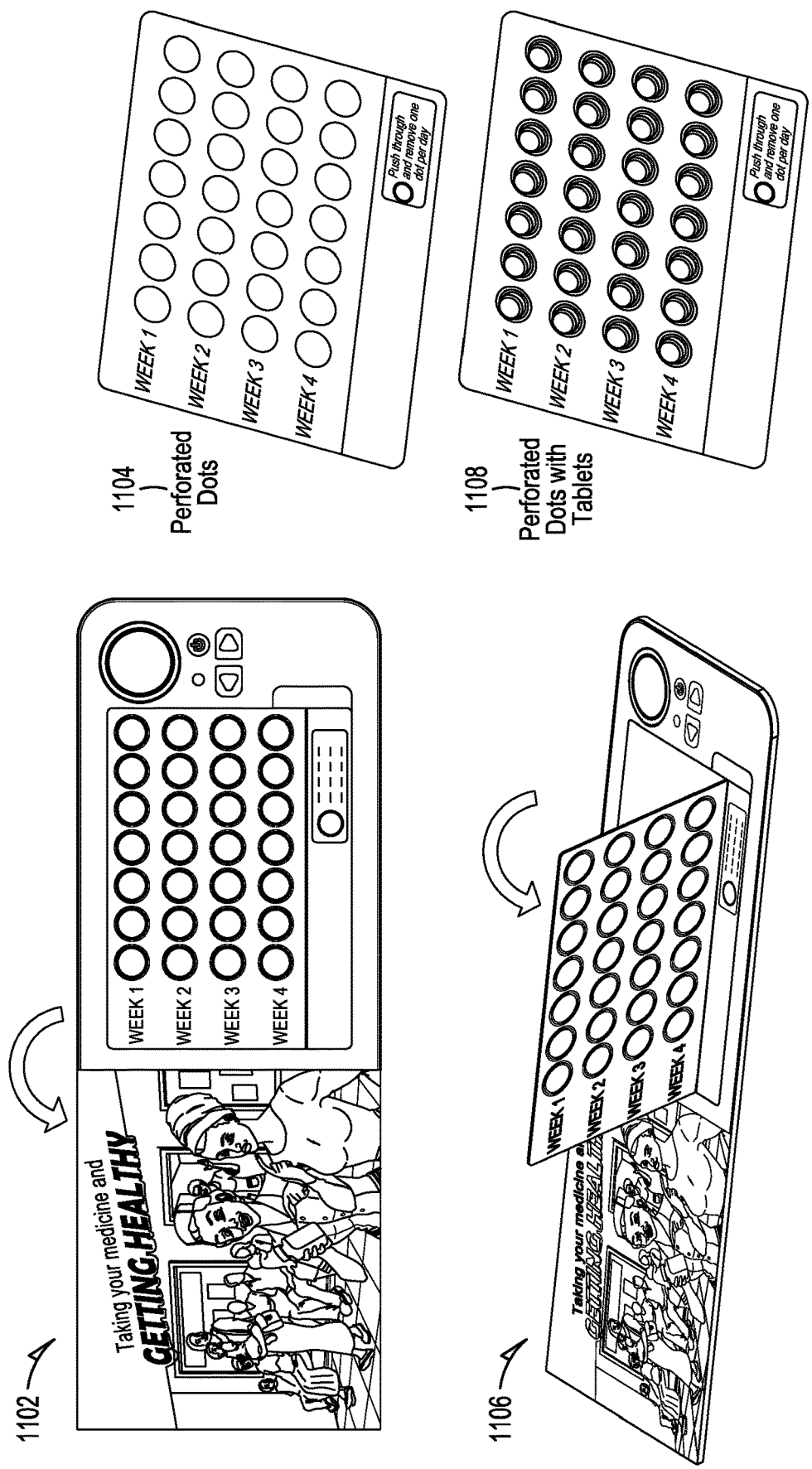
FIG. 11 is a graphical depiction of an example dosage-tracking feature that may be included in a smart booklet.

FIG. 11 is a graphical depiction of an example state-tracking feature that may be included in a smart booklet. In example embodiments, as shown in view 1102, the state-tracking feature allows for daily tracking over particular time periods (e.g., week 1, week 2, week 3, and week 4). In example embodiments, a blister pack or card inserted into the smart booklet has removable portions correspond to each day. In example embodiments, as shown in the view 1106, the state-tracking feature comprises a insertable and removable blister pack (or a card with removable tabs) that may be flipped up or removed for accessing and removing one or more tablets of one or more medicines included in the blister pack or for accessing and removing one or more removable tabs. In example embodiments, as depicted in view 1108, the blister pack may have two layers, including a first layer comprising printed-paper card-stock with perforations (e.g. perforated dots) and a second layer comprising a foil backing. In example embodiments, one or more medicines may be punched out from one or more perforated dots corresponding to one or more containers of the blister-pack. In other embodiments, as depicted in view 1104, the card may simply have a single layer comprising removable tabs (e.g., perforated dots). In example embodiments, an inductive sensor grid senses where foil has been removed from one or more containers. Upon detection of a state change (e.g., corresponding removal of one or more medicines), a set of data items pertaining to monitoring of user behavior or adherence to a treatment and/or educational program by the user is updated, such as a date and time at which it was detected that foil corresponding to one or more containers was modified.

Thus, the system will detect whether there is a card or a tablet/pill blister pack loaded in the book (e.g., using electronic recognition via the sensor grid). The system will also detect when tablets or foil-backed tabs are removed. The system will also recognize a type of blister pack, or even a medication or patient (e.g., based on a smart strip that is included on the blister pack). For example, when a page or card (e.g., a blister pack) is inserted into the smart booklet, a set of tabs associated with the page, such as a set of tabs on an edge of the page (e.g., that is used to anchor or connect the page to the smart booklet) can be electronically recognized (e.g., through shorting and/or other methods) to receive configuration information associated with the page, such as a kind of medications there, what week of a treatment program the page is associated with, a default language to use, and so on. In this way, the content included in the one or more memories of the smart booklet may be appropriately selected to correspond to the page that has been inserted into the smart booklet without the need for a user to perform any manual configuration of the smart booklet. In example embodiments, one or more mechanical controls (e.g., the language selection button 906) may be used to override default settings derived from the smart strip.

Figure 12:
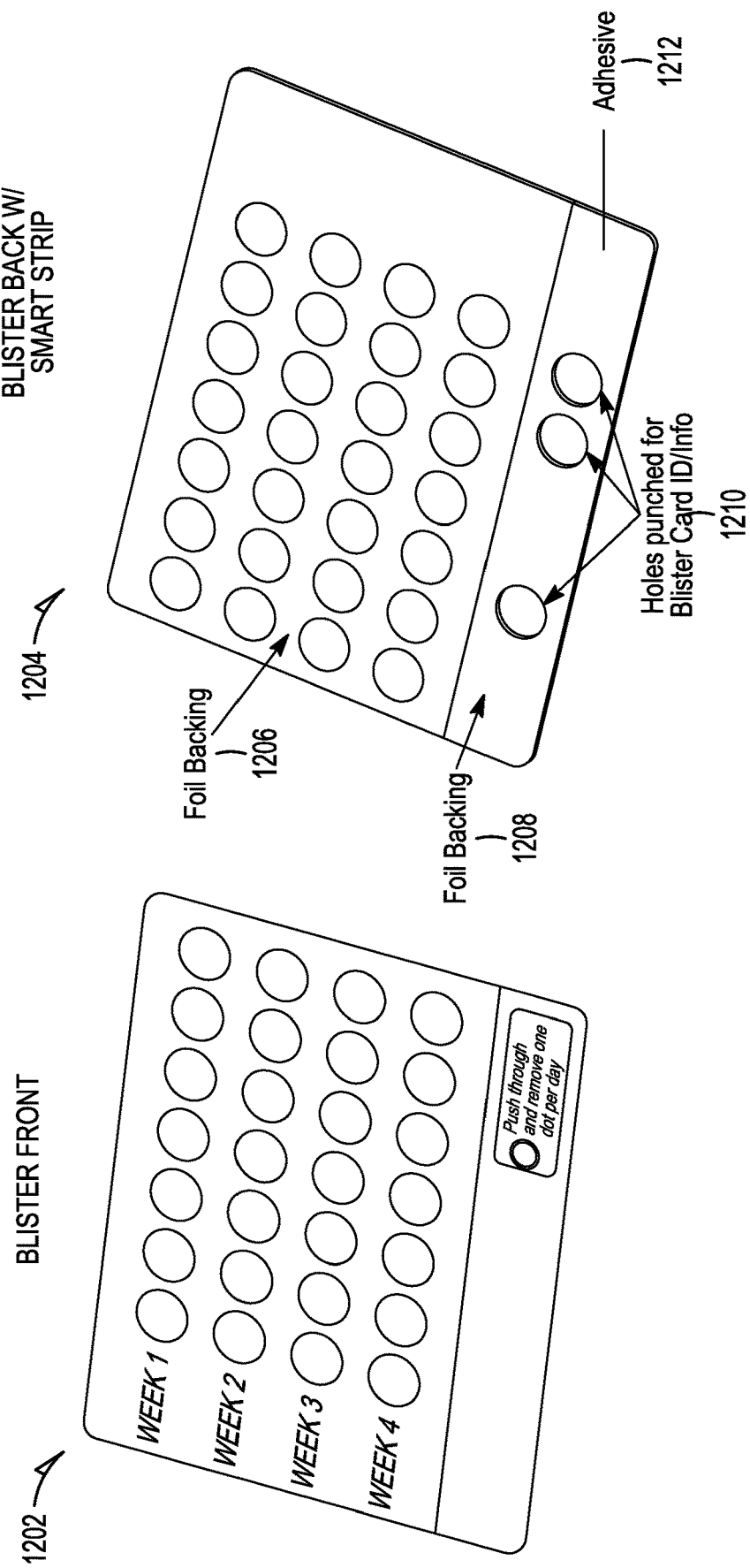
FIG. 12 depicts view of a front and back of a blister pack or card that is insertable into a smart booklet.

FIG. 12 depicts a front of a blister pack or card 1202 that may be inserted into a smart booklet. The blister pack 1202 may further have a crease to facilitate bending the blister (e.g., like a page of book) for accessing tabs or other removable elements included in the blister or card. As depicted in view 1204, the back of the blister pack or card may include a smart strip 1210 into which holes may be punched (e.g., for identifying a type of the blister pack or card). Based on a detection of a type of the type of the card, different rules from a set of rules may be applied to determine messages that are automatically communicated based on the state of the blister pack or card (e.g., to correspond to a particular week of a treatment plan, a stage of maintenance, and so on with which the inserted blister pack or card is associated.) The back of the blister 1204 may include a foil backing 1206 and foil backing 1208 (e.g., to enable inductive sensing of removal of the tabs of the blister pack). The back of the blister pack 1204 may include one or more removable tabs or other connection mechanism for connecting the blister pack to a platform of the smart booklet, as described herein.

Figure 13:
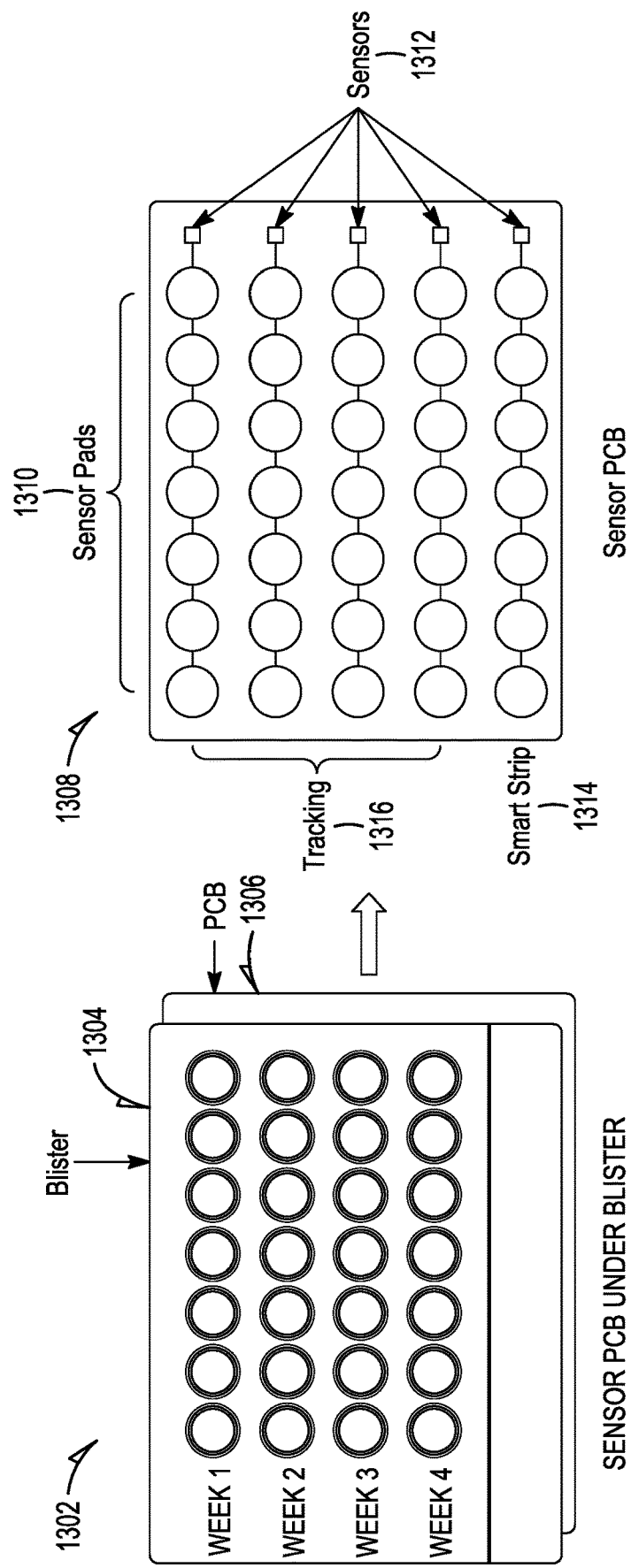
FIG. 13 depicts an interface between the platform of the smart booklet and the blister pack or card that is inserted into the platform.

FIG. 13 depicts an interface between the platform of the smart booklet and the blister pack or card that is inserted into the platform. In example embodiments, the blister 1304 is placed into the smart booklet over a sensor PCB 1306. As shown in 1308, an example sensor PCB includes one or more sensor pads 1310. One set of the sensor pads may be a tracking set 1316, which is used to track changes in the state of the blister pack that is placed over the sensor PCB 1306. Another set of sensor pads may be a smart strip set 1314, which is used to identify a type of blister pack or card that has been inserted into the platform. The sensors 1312 are coupled (e.g., electronically) to the sensor pads (e.g., to sense changes in the state of the blister pack or card) or to identify the blister pack or card based on the smart strip.

Figure 14:
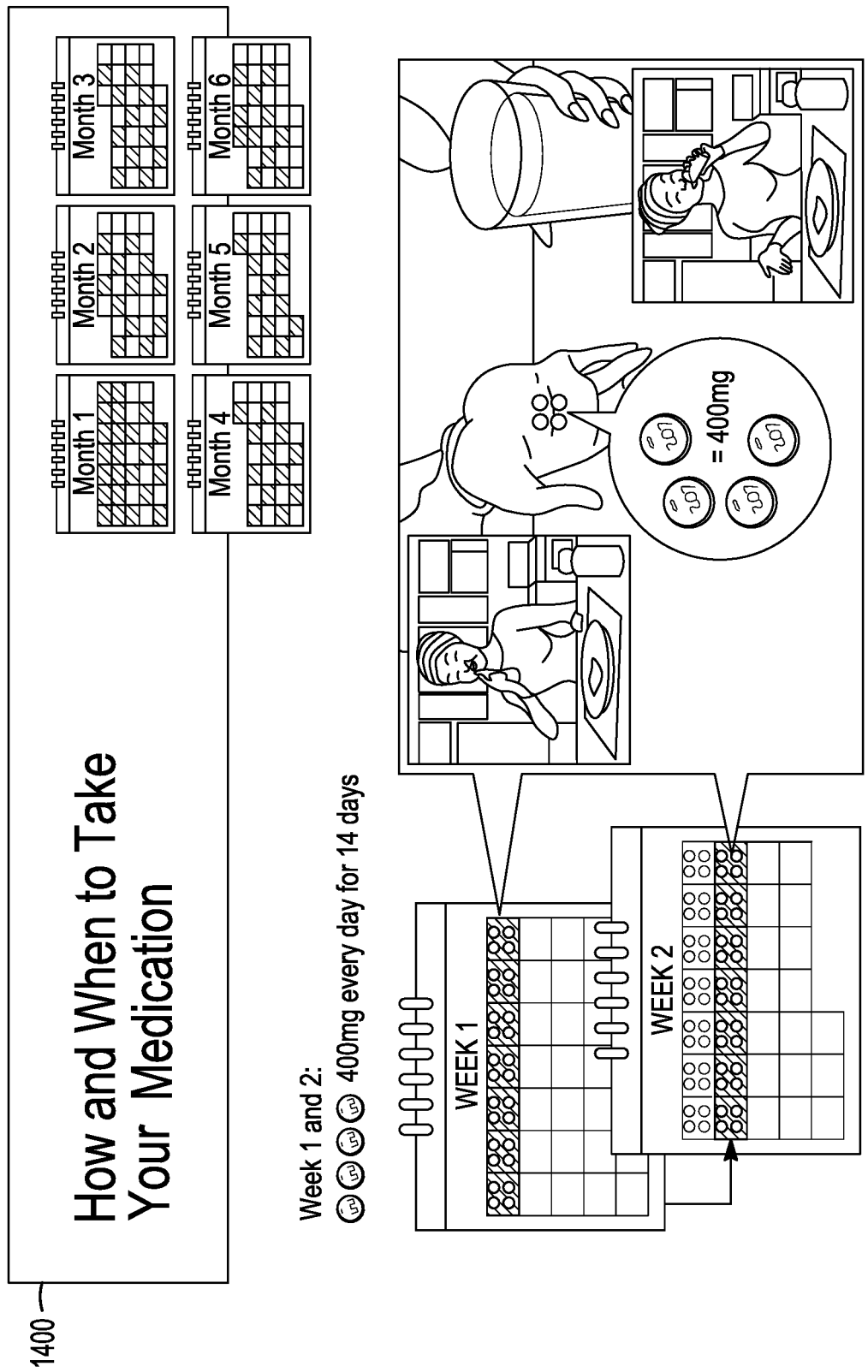
FIG. 14 is a graphical depiction of portions of an example smart booklet that is designed to encourage adherence to a medical treatment plan for Tuberculosis.

FIG. 14 is a graphical depiction of portions of an example smart booklet that is designed to encourage adherence to a medical treatment plan. An illustration is designed to convey educational information pertaining to the number of pills that a patient is to take on each day of a 24-week treatment plan. This illustrated content may be supplemented with one or more audio instructions, as described herein. Furthermore, adherence of the patient to the plan is tracked and customized audio content may be selected and played to assist the patient on how to safely compensate for adherence failures and to encourage the patient to complete the treatment plan, as described herein.

Figure 15:
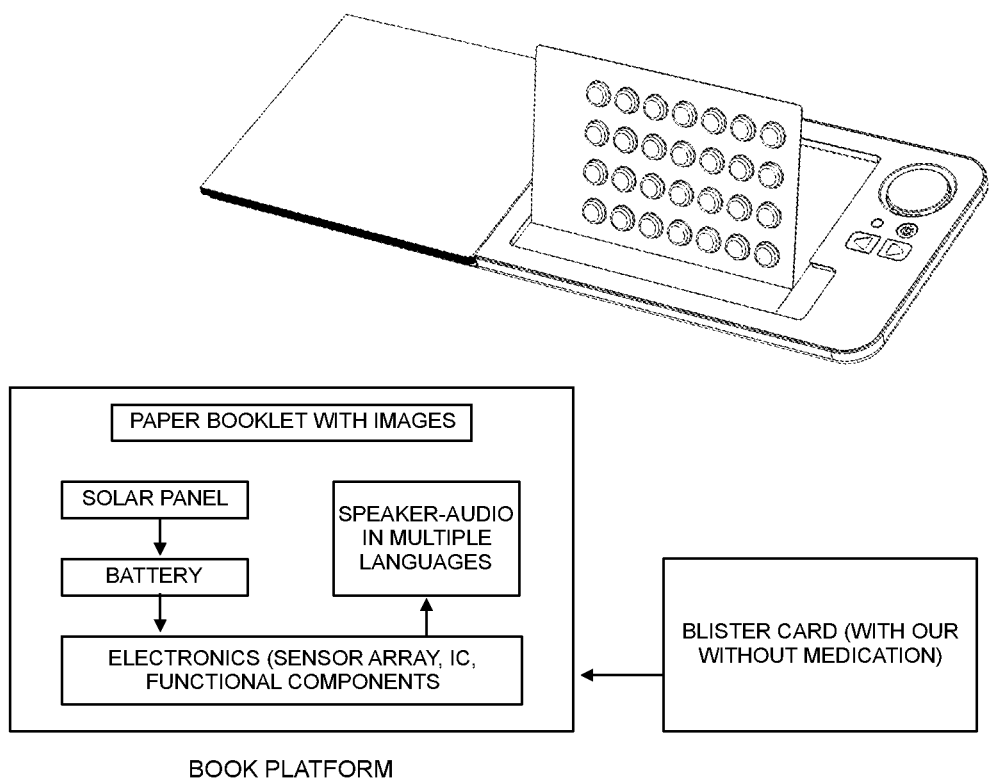
FIG. 15 is a block diagram depicting an example smart booklet platform.

FIG. 15 is a block diagram depicting an example smart booklet platform 1500. In example embodiments, the smart booklet platform includes electronics, including a sensor array, a computer processor (e.g., an integrated circuit), and various functional components (e.g., mechanical buttons)), a battery, a solar panel, and a speaker. Additionally, in example embodiments, the book platform includes one or more components for tracking user behavior, distribution of medicines, and sensing of the distribution of the medicines, such as the blister pack or card described herein and the sensor grid described herein.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the network 104 of FIG. 1) and via one or more appropriate interfaces (e.g., APIs).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 16:
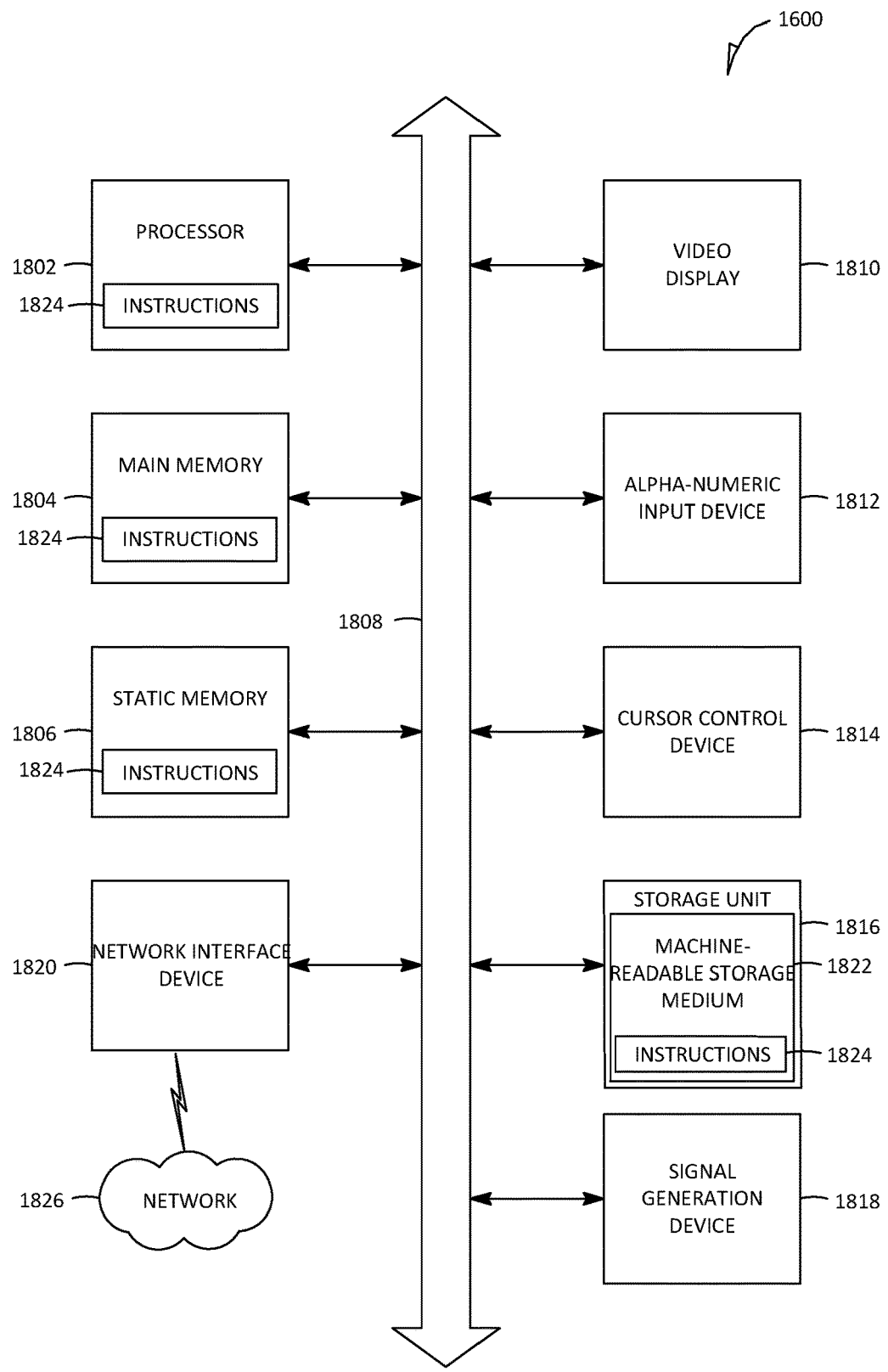
FIG. 16 is a block diagram of machine in the example form of a computer system within which instructions for causing the machine to perform any one or more of the methodologies discussed herein may be executed.

FIG. 16 is a block diagram of machine in the example form of a computer system 1800 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1800 includes a processor 1802 (e.g., a central processing unit (CPU), a graphics processing unit (GPU) or both), a main memory 1804 and a static memory 1806, which communicate with each other via a bus 1808. The computer system 1800 may further include a video display unit 1810 (e.g., a liquid crystal display (LCD) or a cathode ray tube (CRT)). The computer system 1800 also includes an alphanumeric input device 1812 (e.g., a keyboard), a user interface (UI) navigation (or cursor control) device 1814 (e.g., a mouse), a storage unit 1816, a signal generation device 1818 (e.g., a speaker) and a network interface device 1820.

The storage unit 1816 includes a machine-readable storage medium 1822 on which is stored one or more sets of data structures and instructions 1824 (e.g., software) embodying or utilized by any one or more of the methodologies or functions described herein. The instructions 1824 may also reside, completely or at least partially, within the main memory 1804 and/or within the processor 1802 during execution thereof by the computer system 1800, the main memory 1804 and the processor 1802 also constituting machine-readable media. The instructions 1824 may also reside, completely or at least partially, within the static memory 1806.

While the machine-readable storage medium 1822 is shown in an example embodiment to be a single medium, the term "machine-readable storage medium" may include a single medium or multiple media (e.g., a centralized or distributed database, and/or associated caches and servers) that store the one or more instructions 1824 or data structures. The term "machine-readable storage medium" shall also be taken to include any tangible medium that is capable of storing, encoding or carrying instructions for execution by the machine and that cause the machine to perform any one or more of the methodologies of the present embodiments, or that is capable of storing, encoding or carrying data structures utilized by or associated with such instructions. The term "machine-readable storage medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and compact disc-read-only memory (CD-ROM) and digital versatile disc (or digital video disc) read-only memory (DVD-ROM) disks.

Accordingly, a "tangible machine-readable storage medium" may refer to a single storage apparatus or device, as well as "cloud-based" storage systems or storage networks that include multiple storage apparatus or devices. Furthermore, the tangible machine-readable medium is non-transitory in that it does not embody a propagating signal. However, labeling the tangible machine-readable medium as "non-transitory" should not be construed to mean that the medium is incapable of movement—the medium should be considered as being transportable from one physical location to another. Additionally, since the machine-readable storage medium 1822 is tangible, the medium may be considered to be a machine-readable device.

The instructions 1824 may further be transmitted or received over a communications network 1826 using a transmission medium. The instructions 1824 may be transmitted using the network interface device 1820 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium capable of storing, encoding or carrying instructions for execution by the machine, and includes digital or analog communications signals or other intangible media to facilitate communication of such software. The network 1826 may be one of the networks 104.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
one or more memories;
one or more processors;
a set of instructions incorporated into the one or more memories, the set of instructions configuring the one or more processors to perform operations for configuring a smart booklet to monitor behavior or encourage adherence to a treatment and/or educational program, the operations comprising:
based on an activation of a detection feature of the smart booklet, detecting that one or more states of one or more pages of the smart booklet have changed;
updating a set of data items pertaining to the monitoring of the behavior or the adherence to the treatment and/or educational program based on the one or more states of the one or more pages that have changed, the set of data items being stored in the one or more memories; and
based on the updating of the set of data items, applying a set of rules for selecting a notification from a plurality of notifications stored in the one or more memories for communicating the notification via an output component of the smart booklet, wherein removal of a tablet or tab from a card, page, or blister causes removal of a metal foil element from the card, page, or blister and wherein the detection feature detects the removal of the metal foil element.

2. The system of claim 1, wherein the activation of the detection feature is based on a detection of a closing of the smart booklet or a closing or opening of the page of the smart booklet.

3. The system of claim 2, wherein the detection of the closing of the smart booklet or the detecting of the closing or opening of the page of the smart booklet is recognized by an inductive, electronic, or mechanical sensor of the smart booklet.

4. The system of claim 1, wherein a presence of a medicine or a tab included on a removable page or card inserted into the smart booklet is recognized based on an analysis of a type of the removable page or card and input from one or more electronic sensors of the smart booklet.

5. The system of claim 1, wherein the set of rules are configured to identify a failure of the adherence to the treatment program and/or educational program, the set of rules being received from an external system and stored in the one or more memories.

6. The system of claim 1, wherein the set of rules are configured to identify a type of the failure of the adherence to the treatment and/or educational program and select the notification is based on a determination of a locale into which the smart booklet was distributed.

7. A method comprising:
performing operations for configuring a smart booklet to monitor behavior or encourage adherence to a treatment and/or educational program, the operations comprising:
based on an activation of a detection feature of the smart booklet, detecting that one or more states of one or more pages of the smart booklet have changed;
updating a set of data items pertaining to the monitoring of the behavior or the adherence to the treatment and/or educational program based on the one or more states of the one or more pages that have changed, the set of data items being stored in one or more memories; and based on the updating of the set of data items, applying a set of rules for selecting a notification from a plurality of notifications stored in the one or more memories for communicating the notification via an output component of the smart booklet, wherein removal of a tablet or tab from a card, page, or blister causes removal of a metal foil element from the card, page, or blister and wherein the detection feature detects the removal of the metal foil element.

8. The method of claim 7, wherein the activation of the detection feature is based on a detection of a closing of the smart booklet or a closing of the page of the smart booklet.

9. The method of claim 8, wherein the detection of the closing of the smart booklet or the detecting of the closing of the page of the smart booklet is recognized by an inductive, electronic, or mechanical sensor of the smart booklet.

10. The method of claim 7, wherein a presence of a medicine or a tab included on a removable page or card inserted into the smart booklet is recognized based on an analysis of a type of the removable page or card and input from one or more electronic sensors of the smart booklet.

11. The method of claim 7, wherein the set of rules are configured to identify a failure of the adherence to the treatment program and/or educational program, the set of rules being received from an external system and stored in the one or more memories.

12. The method of claim 7, wherein the set of rules are configured to identify a type of the failure of the adherence to the treatment and/or educational program and select the notification is based on a determination of a locale into which the smart booklet was distributed.

13. A non-transitory computer-readable storage medium storing a set of instructions that, when executed by one or more controllers, cause the one or more controllers to perform operations for configuring a smart booklet to monitor behavior or encourage adherence to a treatment and/or educational program, the operations comprising:

based on an activation of a detection feature of the smart booklet, detecting that one or more states of one or more pages of the smart booklet have changed;

updating a set of data items pertaining to the monitoring of the behavior or the adherence to the treatment and/or educational program based on the one or more states of the one or more pages that have changed, the set of data items being stored in one or more memories; and based on the updating of the set of data items, applying a set of rules for selecting a notification from a plurality of notifications stored in the one or more memories for communicating the notification via an output component of the smart booklet, wherein removal of a tablet or tab from a card, page, or blister causes removal of a metal foil element from the card, page, or blister and wherein the detection feature detects the removal of the metal foil element.

14. The non-transitory computer-readable storage medium of claim 13, wherein the activation of the detection feature is based on a detection of a closing or opening of the smart booklet or a closing or opening of the page of the smart booklet.

15. The non-transitory computer-readable storage medium of claim 14, wherein the detection of the closing or opening of the smart booklet or the detecting of the closing or opening of the page of the smart booklet is recognized by an inductive, electronic, or mechanical sensor of the smart booklet.

16. The non-transitory computer-readable storage medium of claim 13, wherein a presence of a medicine or a tab included on a removable page or card inserted into the smart booklet is recognized based on an analysis of a type of the removable page or card and input from one or more electronic sensors of the smart booklet.

17. The non-transitory computer-readable storage medium of claim 13, wherein the set of rules are configured to identify a failure of the adherence to the treatment program and/or educational program, the set of rules being received from an external system and stored in the one or more memories.

* * * * *